United States Patent [19]

Bhongle et al.

[11] Patent Number: 5,554,744
[45] Date of Patent: Sep. 10, 1996

[54] METHOD FOR LOADING SOLID SUPPORTS FOR NUCLEIC ACID SYNTHESIS

[75] Inventors: Nandkumar Bhongle; Jin-Yan Tang, both of Shrewsbury, Mass.

[73] Assignee: Hybridon, Inc., Worcester, Mass.

[21] Appl. No.: 311,156

[22] Filed: Sep. 23, 1994

[51] Int. Cl.[6] .................................................. C07H 21/00
[52] U.S. Cl. .................................................. 536/25.3
[58] Field of Search .................................. 536/22.1, 25.3

[56] References Cited

U.S. PATENT DOCUMENTS 5,149,798  9/1992  Agrawal et al. ........................ 536/25.3

OTHER PUBLICATIONS

Zamecnik and Stephenson, *Proc. Natl. Acad. Sci. USA* 75, 280–284 (1978).
Agrawal et al., *Trends in Biotech.* 10, 152–158 (1992).
Uhlmann and Peyman, *Chem. Rev.* 90, 543 (1990).
See generally, *Methods in Molecular Biology, vol. 20: Protocols for Oligonucleotides and Analogs* (S. Agrawal, Ed. Humana Press (1993)).
See generally, *Oligonucleotides and Analogues: A Practical Approach* (F. Eckstein, Ed. (1991)).
Khorana et al., *J. Molec. Biol.* 72, 209 (1972).
Reese, *Tetrahedron Lett.* 34, 3143–3179 (1978).
Beaucage and Caruthers, *Tetrahedron Lett.* 22, 1859–1862 (1981).
Agrawal and Goodchild, *Tetrahedron Lett.* 28, 3539–3542 (1987).
Connolly et al., *Biochemistry* 23, 3443 (1984).
Jager et al., *Biochemistry* 27, 7237 (1988).
Agrawal et al., *Proc. Natl. Acad. Sci. USA* 85, 7079–7083 (1988).
Pon, "Solid Phase Supports for Oligonucleotide Synthesis," *Methods in Molec. Biol., vol. 20: Protocols for Oligonucleotides and Analogs*, p. 465 (Agrawal, Ed. Humana Press (1993)).
Sproat and Gait, in *Oligonucleotide Synthesis: A Practical Approach*, pp. 83–115 (Gait, Ed., IRL Press, 1984).
Koster et al., *Tetrahedron* 40, 103–112 (1984).
Gough et al., *Tetrahedron Lett.* 22, 4177–4180 (1981).
Kierzek, *Biochemistry* 25, 7840–7846 (1986).
Montserrat et al., *Nucleosides & Nucleotides* 12, 967 (1993).
Pon et al., *Biotechniques* 6, 768–775 (1988).
Damha et al., *Nucleic Acid Res.* 18, 3813–3821 (1990).
Tong et al., *J. Org. Chem.* 58, 2223–2231 (1993).

*Primary Examiner*—John W. Rollins
*Attorney, Agent, or Firm*—Banner & Allegretti, Ltd.

[57] ABSTRACT

New methods of loading solid supports for oligonucleotide synthesis are presented. The new methods comprise coupling a succinylated nucleoside to a solid support using diisopropylcarbodiimide (DIC) as an activator and N-hydroxybenzotriazole (HOBT) as an acid catalyst. DIC is substantially cheaper than the currently used activating agent, 1-(3-dimethylaminopropyl)-3-ethylcarbodiimide (DEC). Furthermore, in the preferred embodiment, when it is used in combination with HOBT, coupling is more efficient, requiring less nucleoside to achieve the same loading densities as in the prior art. The loading process is faster than prior art methods and the overall cost savings of about 43% are realized.

27 Claims, No Drawings

METHOD FOR LOADING SOLID SUPPORTS FOR NUCLEIC ACID SYNTHESIS

BACKGROUND OF THE INVENTION

1. Field of the Invention

This invention relates to the field of oligonucleotide synthesis, and, more particularly, to methods of loading mononucleosides on a solid support.

2. Description of the Related Art

Since Zamecnik and Stephenson, *Proc. Natl. Acad. Sci. USA* 75, 280–284 (1978) first demonstrated virus replication inhibition by synthetic oligonucleotides, great interest has been generated in oligonucleotides as therapeutic agents. In recent years the development of oligonucleotides as therapeutic agents and as agents of gene expression modulation has gained great momentum. The greatest development has been in the use of so-called antisense oligonucleotides, which form Watson-Crick duplexes with target mRNAs. Agrawal, *Trends in Biotechnology* 10, 152–158 (1992), extensively reviews the development of antisense oligonucleotides as antiviral agents. See also Uhlmann and Peymann, *Chem. Rev.* 90, 543 (1990).

Various methods have been developed for the synthesis of oligonucleotides for such purposes. See generally, *Methods in Molecular Biology, Vol. 20: Protocols for Oligonucleotides and Analogs* (S. Agrawal, Ed., Humana Press, 1993); *Oligonucleotides and Analogues: A Practical Approach* (F. Eckstein, Ed., 1991); Uhlmann and Peyman, supra. Early synthetic approaches included phosphodiester and phosphotriester chemistries. Khorana et al., *J. Molec. Biol.* 72, 209 (1972) discloses phosphodiester chemistry for oligonucleotide synthesis. Reese, *Tetrahedron Lett.* 34, 3143–3179 (1978), discloses phosphotriester chemistry for synthesis of oligonucleotides and polynucleotides. These early approaches have largely given way to the more efficient phosphoramidite and H-phosphonate approaches to synthesis. Beaucage and Caruthers, *Tetrahedron Lett.* 22, 1859–1862 (1981), discloses the use of deoxynucleoside phosphoramidites in polynucleotide synthesis. Agrawal and Zamecnik, U.S. Pat. No. 5,149,798 (1992), discloses optimized synthesis of oligonucleotides by the H-phosphonate approach.

Both of these modern approaches have been used to synthesize oligonucleotides having a variety of modified internucleotide linkages. Agrawal and Goodchild, *Tetrahedron Lett.* 28, 3539–3542 (1987), teaches synthesis of oligonucleotide methylphosphonates using phosphoramidite chemistry. Connolly et al., *Biochemistry* 23, 3443 (1984), discloses synthesis of oligonucleotide phosphorothioates using phosphoramidite chemistry. Jager et al., *Biochemistry* 27, 7237 (1988), discloses synthesis of oligonucleotide phosphoramidates using phosphoramidite chemistry. Agrawal et al., *Proc. Natl. Acad. Sci. USA* 85, 7079–7083 (1988), discloses synthesis of oligonucleotide phosphoramidates and phosphorothioates using H-phosphonate chemistry.

Solid phase synthesis of oligonucleotides by the foregoing methods involves the same generalized protocol. Briefly, this approach comprises anchoring the 3'-most nucleoside to a solid support functionalized with amino and/or hydroxyl moieties and subsequently adding the additional nucleosides in stepwise fashion. Desired internucleoside linkages are formed between the 3' functional group of the incoming nucleoside and the 5' hydroxyl group of the 5'-most nucleoside of the nascent, support-bound oligonucleotide.

Oligonucleotide synthesis generally begins with coupling, or "loading," of the 3'-most nucleoside of the desired oligonucleotide to a functionalized solid phase support. A variety of solid supports and methods for their preparation are known in the art. E.g., Pon, "Solid-Phase Supports for Oligonucleotide Synthesis," in *Methods in Molec. Biol., Vol. 20: Protocols for Oligonucleotides and Analogs*, p. 465 (Agrawal, Ed., Humana Press, 1993). Generally, the functionalized support has a plurality of long chain alkyl amines (LCAA) on the surface that serve as sites for nucleoside coupling. Controlled pore glass (CPG) is the most widely used support. It consists of approximately 100–200 μm beads with pores ranging from a few hundred to a few thousand angstroms.

CPG supports are generally loaded by attaching a nucleoside-3'-succinate to the support through the succinyl group via an amide bond. Early efforts used dicyclohexylcarbodiimide (DCC) to activate the nucleoside-3'-succinate. Activation was accomplished by converting the nucleoside-3'-succinate into the symmetrical anhydride (Sproat and Gait, in *Oligonucleotide Synthesis: a Practical Approach* p. 83–115 (Gait, Ed., IRL Press, 1984)), or esterifying with p-nitrophenol (Atkinson and Smith, id. at 35–81; Koster et al., *Tetrahedron* 40, 103–112 (1984)) or pentachlorophenol (Gough et al, *Tetrahedron Lett.* 22, 4177–4180 (1981); Klerzek, *Biochem.* 25, 7840–7846 (1986)).

Montserrat et al., *Nucleosides & Nucleotides* 12, 967 (1993) reported that DCC and 1-hydoxybenzotriazole (HOBT) (used in equimolar amounts in a 14:1 dichloromethane/dimethylformamide solvent) resulted in higher loading densities than when DCC was used alone.

The use of DCC suffers from a number of disadvantages, however. First, DCC is highly toxic. Second, loading was tedious and gave only moderate yields (50–75%). Third, the coupling reactions were lengthy, requiring 3–4 d to make the activated succinates and an additional 4–7 d to couple them to the CPG. And finally, loading values were quite variable, and optimum loading of 30–40 μmol/g was not always obtained.

Pon et al., *Biotechniques* 6, 768–775 (1988), improved on this method by employing 1-(3-dimethylaminopropyl)-3-ethylcarbodiimide (DEC). Using this reagent along with a catalytic amount of dimethylaminopyridine (DMAP) in triethylamine/pyridine, Pon et al. observed direct coupling of the nucleoside-3'-succinate to the support. DEC, a smaller, less rigid carbodiimide (compared to DCC) was found to give much better results—loadings of up to 50–60 μmol/g could be obtained in 24 hours.

In an alternative procedure, Damha et al., *Nucl. Acids Res.* 18, 3813–3821 (1990), showed that loading could be accomplished by succinylating the LCAA of the solid support, thereby providing a carboxylic acid functional group, followed by direct attachment of a nucleoside by esterification with DEC and DMAP in pyridine.

Tong et al., *J. Org. Chem* 58, 2223 (1993), followed the approach of Damha et al., supra, and compared the efficiency of DCC, DEC, and DIC in loading 3' unprotected cytidine onto a succinylated CPG support under basic conditions. The reaction was conducted in the presence of DMAP in dry pyridine. Loadings of 22 (DCC), 18 (DEC), and 30 (DIC) μmol/g were obtained.

A major drawback of the current methods for loading solid support is that the main solvent is pyridine. Pyridine is toxic, has an obnoxious odor, and, therefore, is a work place and environmental hazard. In addition, DEC is costly, particularly when used in a large, production scale syntheses. Consequently, improved methods of column loading for oligonucleotide synthesis are desirable.

SUMMARY OF THE INVENTION

The present invention comprises new and improved methods of loading nucleosides onto a solid support for solid phase oligonucleotide synthesis. The methods of the present invention provide several advantages over prior art methods. First, they are more cost efficient. Cheaper, more efficient catalysts and activators used in the present invention result in cost savings as lesser amounts of both catalyst and mononucleoside reactant are required. Savings of approximately 43% have been observed for loading densities of about 70–80 µmol/g. Second, we are able to eliminate pyridine as a solvent, which not only effects cost savings, but improves the safety of the process, both to the worker and to the environment. Concomitantly, fewer hazardous wastes are produced.

In a first aspect of the present invention, diisopropylcarbodiimide (DIC) is used as an activator in the acid catalyzed loading of succinylated mononucleoside. It has been unexpectedly found that the use of DIC in acid catalyzed loading is more effective than standard techniques using DEC; DIC is also more effective than DEC in acid catalyzed loading. DIC offers the further advantage of being cheaper per unit mass. DEC presently costs about $308/100 g while DIC costs about $97/100 g. In addition, DIC can be used in an amount that is about 20% that of DEC.

In a second aspect of the present invention, 1-hydoxybenzotriazole (HOBT) is used in combination with DIC to catalyze linkage of a mononucleoside to an activated solid support. HOBT acts more efficiently and economically than other compounds such as N-hydroxysuccinimide (NHS), paratoluenesulfonic acid (pTSA), and trifluoroacteic acid (TFA). Loading densities approaching 120 µmol/g on controlled pore glass (CPG) solid support are readily obtained. Higher loading densities are also observed on other solid supports such as the "TENTAGEL" (Rapp Polymere) and "HLP" (ABI). Nitrobenzotriazole (NBT) acts as efficiently as HOBT, but is somewhat more expensive.

In a the third aspect of the present invention, a method is presented for loading a non-linker-attached nucleoside (i.e., a nucleoside having a free 3' hydroxyl group) onto a solid support bearing a linker groug, e.g., a succinyl moiety. In this aspect of the invention, a solid support to which a linker has been attached is loaded by contacting it with a nucleoside having a free 3' hydroxyl group in the presence of DIC and HOBT.

In the fourth aspect of the present invention pyridine is eliminated as a solvent. Pyridine has generally been used in the loading process as a solvent and to dissolve and wash away all catalyst, unreacted starting materials, and reaction by-products. Because of pyridine's toxicity, its elimination from the loading process increases the safety of the process. In addition, fewer environmentally hazardous wastes are produced. We have found that acetonitrile can be used in place of pyridine without affecting loading efficiencies. Cost savings are also thereby realized.

Another benefit provided by the methods of the present invention is the ability to adjust loading densities to any desired level, up to the maximum possible empirical value obtainable under optimal conditions. This is useful because equipment limitations (and/or other factors) may restrict the degree of loading to values substantially less than the empirical maximum.

The present methods can be used to load any nucleoside onto any functionalized solid support. The nucleoside may comprise any unmodified base (e.g., A, T, C, G, or U) or modified base, and a modified or unmodified ribose moiety. Any solid support suitable for use in oligonucleotide synthesis can be used with the present methods.

The foregoing merely summarizes certain aspects of the present invention and is not intended, nor should it be construed, to limit the invention in any manner.

All patents and publications cited in this specification are hereby incorporated by reference in their entirety.

DETAILED DESCRIPTION OF THE PREFERRED EMBODIMENTS

The present invention comprises new methods for loading mononucleosides on a solid support. As used herein "loading" refers to the chemical linkage of a nucleoside (which will be the 3'-most nucleoside of the oligonucleotide to be synthesized) to a functional group on a solid support. The degree of loading is expressed in µmol monomer/g solid support. A "functional group" is a chemical moiety, such as an amino or hydroxyl moiety, capable of being joined to a nucleoside either directly or via a linker. A "functionalized support" is a support having such functional groups.

Current methods of loading solid supports are slow, often taking up to about one week to load a controlled pore glass (CPG) support, and require about 90–100 g (or about 0.15 mol) of DMT-protected succinylated monomer to load 500 g of CPG. Typical maximum loading densities are about 75 µmol/g. While loading in a 24 hour period has been reported, the loading densities are typically low. The methods presented herein substantially improve on these values. We have found that we are able to obtain loading densities in the range of 70 to 80 µmol/g using one third of the amount of DMT-protected succinylated monomer and that by increasing the amount of DMT-protected succinylated monomer, activator, and catalyst, loading densities of about 120 µmol/g are easily obtained on CPG. We have observed higher loading densities on other supports having a greater concentration of functional groups. In addition to achieving higher loading densities, the new methods are faster as well, allowing complete loading of the column (with high loading density) in just two days. Thus, use of the methods disclosed herein will substantially reduce costs and time.

The new methods disclosed herein are also significantly less hazardous for the worker and safer for the environment. Pyridine is currently used as a reaction solvent and, alone or in combination with other solvents, to wash away unreacted reactants, catalyst, and unwanted reaction by-products. We have found that the amount of pyridine can be reduced to about 5% in acetonitrile or eliminated completely. Because pyridine is toxic and has an obnoxious odor, the present methods are less hazardous than the prior art methods.

The present methods also require lesser amounts of reagents, resulting in lesser costs and amounts of waste. We have found that column loading densities in the range of about 70–80 µmol/g can be attained using less than about $3 \times 10^{-3}$ mol of nucleoside per 25 g of CPG. Thus, the current methods provide additional cost savings by these means as well. Overall, savings of about 43% are realized with the new methods for loading densities in the range of about 70–80 µmol/g.

The present invention provides methods of loading a functionalized solid support for oligonucleoside synthesis comprising contacting the functionalized solid support with a solvent, diisopropylcarbodiimide, and a nucleoside having a 3' linker group attached at a pH of less than 7.0.

In the first embodiment of the invention, diisopropylcarbodiimide (DIC) is used as an activator for the acid catalyzed loading of nucleoside-3'-succinates. The activator forms an intermediate with the terminal carboxylic acid moiety of the nucleoside-3'-succinate, rendering it susceptible to nucleophilic attack by a support-bound amino functional group. It has been unexpectedly found that DIC in the presence of 1-hydroxybenzotirazole (HOBT) is more effective than DEC at activating the succinyl carboxylic acid moiety. Under ideal conditions, wherein the coupling of the nucleoside-3'-succinate to the solid support is 100% complete, 1 equivalent of DIC is required to couple 1 equivalent of nucleoside-3'-succinate to the support. DIC is moisture sensitive, however, and therefore, in general, more than 1 equivalent is required. This will not detract appreciably from the cost benefit of using DIC since it is substantially cheaper than DEC. We have found that about 2.5 to 3.0 eq of DIC per 1 eq of mononucleoside succinate results in excellent loading, routinely yielding loading densities of about 75 to about 85 μmol/g.

In the second embodiment of the invention, HOBT is used to catalyze DIC activated loading. Experiments using pyridine as a solvent (presented infra) demonstrate that HOBT is a more effective than other compounds such as N-hydroxysuccinimide (NHS), paratoluenesulfonic acid (pTSA), and trifluoroacetic acid (TFA). Our experiments demonstrate that the use of HOBT results in loading densities ranging from 30 to 100% greater than those attained using NHS, pTSA, and TFA. The amount of HOBT is not critical; it should be sufficient to catalyze the reaction. We have found that about 0.08 to about 0.16 g HOBT per ml DIC work exceedingly well, although lesser or greater amounts are likely to work just as well. Most preferably, a lesser amount of HOBT is used, generally about 0.08 g.

In another aspect of this embodiment, nitro-HOBT is used as a catalyst. Our experiments show that catalysis with nitro-HOBT results in essentially equivalent loading densities as compared to when HOBT is used. Nitro-HOBT is used in the amount as described above for HOBT.

The methods of the present invention can also be used to load a non-linker-attached nucleoside (i.e., a nucleoside having a free 3' hydroxyl group) onto a column bearing a linker groug, e.g., a succinyl moiety. Accordingly, in a third embodiment of the present invention, a solid support to which a linker, most preferably succinic acid, has been attached is loaded by contacting it with a nucleoside having a free 3' hydroxyl group in the presence of DIC and HOBT. The conditions for this reaction are the same as described herein for the loading of nucleosides bearing a 3' linker onto functionalized supports.

In a fourth embodiment of the present invention, methods of loading a solid support are presented in which the amount of pyridine used as the reaction solvent and wash solvent is substantially reduced or eliminated. We have found that pyridine need not be the main solvent in the loading reaction. Any solvent that dissolves the reactants but does not react itself can be used. We have found that both acetonitrile and dichloromethane are suitable solvents. Acetonitrile is the most preferred solvent. In one aspect of this embodiment, a mixture of pyridine with acetonitrile and/or dichloromethane is used as the primary solvent for loading nucleosides. A small amount of pyridine (e.g., about 5%) may be used to ensure a minimal amount of detritylation, but is not required. Accordingly, in another aspect of this embodiment, no pyridine is used. Because of the reduced costs, in the most preferred embodiment the solvent is acetonitrile with very little (e.g., 5% or less) or no pyridine.

The present invention can be used with any functionalized solid support. A number of such supports are known in the art. E.g., Pon in *Methods in Molec. Biol.*, supra. We demonstrate below that both "TENTAGEL S" (Rapp Polymere, Tübingen, Germany)(a support in which polyethyleneglycol spacers are grafted on a gel-type support) and HLP (ABI, Foster City, Calif.) (a PEG-Polystyrene support) can be loaded with the current methods to extremely high densities. CPG is the most preferred support for DNA synthesis.

While the results presented below were obtained using succinylated thymidine monomer, those skilled in the art will appreciate that any suitably protected nucleoside monomer (naturally occurring or modified) can be used with the present methods. Dimer blocks and other multinucleoside synthons can also be loaded according to the methods of the present invention. In addition, although succinic acid is the preferred linker, any suitable linker can be used. Such a linker will preferably have a free carboxyl group that a support-bound amino group can attack to form an amide bond, thereby binding the linker and its attached nucleoside to the support. Examples of alternative linkers are disclosed by Pon in *Methods in Molec. Biol.*, supra.

The following Examples are intended for illustrative purposes and are not intended, nor should they be construed, as limiting the invention in any way.

EXAMPLES

Example 1

Standard Method of Loading of DMT-dT-Succinic Acid on Controlled Pore Glass 500 g of CPG (Schott, Hozheim, Germany) (particle size: 100–130 μm; pore size: $D_{50}$: 41.6 nm), 6.1 g of dimethylamino pyridine (Aldrich, Milwaukee, Wis.), 50 g of triethylamine (Aldrich), and 100 g of ethyl-3-(3-dimethylamino propyl)carbodiimide (DEC, mol. wt. 191.7) (Sigma, St. Louis, Mo.) were placed in a 5 l Schott bottle and hand shaken for 20 minutes. 60 g of DMT-dT-succinic acid (Monomer Sciences, Huntsville, Ala.) was added and the bottle capped and shaken in an orbital shaker at 160 rpm for 18 hours.

A small analytical sample of the resin was withdrawn from the Schott bottle, successively washed with pyridine (3×5 ml) (Baxter, Muskegon, Mich.), methanol (3×5 ml) (Baxter), and methylene chloride (3×5 ml) (EM Science, Cincinnati, Ohio) successively, and dried in vacuo.

Approximately 20 mg of dry resin was weighed, 200 μl perchloric acid/ethanol (6:4) was added, and the resulting solution diluted to 100 ml with methylene chloride. The absorbance was measured at 498 nm. The same procedure was repeated on a second analytical sample and the average loading value calculated using Beer's law with a molar absorption coefficient of 70 l/(mol cm) for DMT. A loading value of 66.7 μmol/g was obtained.

An additional 20.0 g of DMT-dT-succinic acid was added to the Schott bottle and the mixture shaken for 18 hours at ambient temperature. Another analytical sample was removed and worked-up as described above. The absorbance of the sample was measured and a loading value of 66.5 µmol/g obtained.

Another 20.0 g of DMT-dT-succinic acid was added to the Schott bottle and the mixture shaken for 18 hours at ambient temperature. A third analytical sample was removed and worked-up as described above. The absorbance of the sample was measured and a loading value of 69.6 µmol/g obtained.

The mixture remaining in the Schott bottle was filtered and the resin washed with pyridine (3×1 l). The dry solid was transferred to a Schott bottle and Cap A (1.0 l of acetic anhydride in tetrahydrofuran) (Cruachem, Linvingstone, United Kingdom) and Cap B (1.5 l of N-methylimidzole, pyridine in tetrahydrofuran) (Millipore, Bedford, Mass.) were added. The mixture was shaken for 18 hours at ambient temperature. The solid (CPG-T) was filtered and successively washed with methanol (3×1 l) and methylene chloride (3×1 l) and dried in vacuo to yield 502.5 g. The resin was subjected to the same procedure described above for each of the small samples. A loading value of 71.4 µmol/g was obtained.

Example 2

New Method of Loading DMT-dT-Succinic Acid on Controlled Pore Glass 250.0 g of CPG (Schott), 0.8 g of hydroxybenzotriazole (mol. wt. 135.13) (Aldrich), and 10 ml of 1,3-diisopropyl-carbodiimide (DIC, mol. wt. 126.20, density=0.806 g/ml) (Aldrich) were mixed with 50 ml of pyridine (Baxter) and 1 l of acetonitrile (Baxter) in a 2 l Schott bottle and shaken for 20 minutes. 15 g of DMT-T-succinic acid (mol. wt. 644) (Monomer Sciences) were added, the bottle stoppered and shaken in an orbital shaker at a rate of 180 rpm for 16 hours.

A small analytical sample of the resin was withdrawn from the Schott bottle and washed with 5% pyridine in acetonitrile (3×5 ml), methanol (3×5 ml), and methylene chloride (3×5 ml) successively and dried under a stream of in vacuo.

Approximately 20 mg of the dry resin were weighed and 200 ml perchloric acid/ethanol (6:4) added. The solution was diluted to 70 ml with methylene chloride and the absorbance measured at 498 nm. The entire procedure was repeated and the average value of the absorbencies used to calculate the loading. The loading was calculated as above. An average loading value of 78.0 µmol/g was obtained.

The remaining solution in the Schott bottle was filtered and washed with 5% pyridine in acetonitrile (3×500 ml). Dry solid was transferred to a Schott bottle and Cap A (500 ml) and Cap B (750 ml) (Cap A and Cap B were as described above) were added and the mixture shaken for 16 hours at ambient temperature. The solid (CPG-T) was filtered, washed successively with methanol (3×500 ml) and then methylene chloride (3×500 ml), and dried in vacuo to yield 250 g of CPG-T. The loading value, 78 µmol/g, was calculated as described above.

This entire procedure was repeated, substituting varying amounts of the reactants and using several catalysts and supports. The results are present in Table 1.

From the foregoing it will be appreciated that although specific embodiments of the present invention have been described herein for the purposes of illustration, various modification may be made without deviating from the spirit or scope of the invention.

TABLE 1

| Expt # | CPG (g) | Schott Lot # | Pyridine (ml) | CH₃CN (ml) | DMT-T-SA[c] (g) | DIC (ml) | DEC (g) | HOBT (g) | NBT (g) | NHS (g) | pTSA (g) | TFA (g) | Load (µmol/g) |
|---|---|---|---|---|---|---|---|---|---|---|---|---|---|
| 1 | 500 | 100004 | 2500 | — | 90 | — | 100 | — | — | — | — | — | 73 |
| 2 | 25.0 | " | 125 | — | 2.6 | 6.2 | — | — | — | — | — | — | 31.7 |
| 3 | " | " | " | — | " | " | — | 1.0 | — | — | — | — | 81.5 |
| 4 | " | " | " | — | " | " | — | — | — | 1.0 | — | — | 62.8 |
| 5 | " | " | " | — | " | " | — | — | — | — | 1.0 | — | 24.1 |
| 6 | " | " | " | — | " | " | — | — | — | — | — | 1.0 | 36.3 |
| 7 | " | " | 12 | 113 | " | " | — | 1.0 | — | — | — | — | 112.5 |
| 8 | " | " | 6 | 115 | " | " | — | " | — | — | — | — | 114.6 |
| 9 | " | " | " | " | 1.3 | " | — | " | — | — | — | — | 67.2 |
| 10 | " | " | " | " | 2.6 | " | — | 0.50 | — | — | — | — | 119.5 |
| 11 | 250 | " | 50 | 1000 | 15.0 | 20 | — | 1.60 | — | — | — | — | 77.9 |
| 12 | 25 | 1100002 | 5 | 1000 | 1.5 | 2 | — | 0.16 | — | — | — | — | 86.0 |
| 13 | 25 | " | 5 | 100[d] | 1.5 | 2 | — | " | — | — | — | — | 80.5 |
| 14 | 250 | " | 50 | 1000 | 15.0 | 10 | — | 0.80 | — | — | — | — | 78 |
| 15 | 25 | " | 0 | 100 | 1.5 | 1 | — | 0.08 | — | — | — | — | 80.6 |
| 16 | 25 | " | 5 | 100 | 1.5 | 1 | — | — | 0.08 | — | — | — | 76.3 |
| 17 | 50[a] | — | 10 | 300 | 6.0 | 8 | — | 0.64 | — | — | — | — | 145 |
| 18 | 5.9[b] | — | 5 | 50 | 1.0 | 2 | — | 0.16 | — | — | — | — | 187 |

[a]"TENTAGEL" (Rapp Polymere)
[b]HLP, ABI
[c]DMT-T- Succinic Acid
[d]CH₂Cl₂

What is claimed is:

1. A method of loading a functionalized solid support for oligonucleotide synthesis comprising simultaneously contacting in a solvent the functionalized solid support with diisopropylcarbodiimide, a nucleoside having a 3' linker group attached, and an acid catalyst.

2. The method of claim 1 wherein the acid catalyst is N-hydroxybenzotriazole or nitrohydroxybenzotriazole, or a combination thereof.

3. The method of claim 2 wherein the solid support is

CPG and less than about $3\times10^{-3}$ mol of nucleoside is used per 25 g of CPG.

4. The method of claim 3 wherein about 2 to about 3 moles of diisopropylcarbodiimide are used per mole of nucleoside.

5. The method of claim 4 wherein the amount of N-hydroxybenzotriazole or nitrohydroxybenzotriazole, or combination thereof is about 0.1 times that of the diisopropylcarbodiimide.

6. The method of claim 2 wherein the solvent comprises about 5% or less pyridine.

7. The method of claim 6 wherein the solid support is CPG and less than about $3\times10^{-3}$ mol of nucleoside is used per 25 g of CPG.

8. The method of claim 7 wherein about 2 to about 3 moles of diisopropylcarbodiimide are used per mole of nucleoside.

9. The method of claim 8 wherein the amount of N-hydroxybenzotriazole or nitrohydroxybenzotriazole, or combination thereof is about 0.1 that of the diisopropylcarbodiimide.

10. The method of claim 2 wherein the solvent contains no pyridine.

11. The method of claim 10 wherein the solid support is CPG and less than about $3\times10^{-3}$ mol of nucleoside is used per 25 g of CPG.

12. The method of claim 11 wherein about 2 to about 3 moles of diisopropylcarbodiimide are used per mole of nucleoside.

13. The method of claim 12 wherein the amount of N-hydroxybenzotriazole or nitrohydroxybenzotriazole, or combination thereof is about 0.1 that of the diisopropylcarbodiimide.

14. A method of loading a functionalized solid support for oligonucleotide synthesis comprising simultaneously contacting in a solvent a functionalized solid support having a linker moiety with diisopropylcarbodiimide, a nucleoside having a free 3' hydroxy group, and an acid catalyst.

15. The method of claim 14 wherein the acid catalyst is N-hydroxybenzotriazole or nitrohydroxybenzotriazole, or a combination thereof.

16. The method of claim 15 wherein the functionalized solid support is CPG.

17. The method of claim 16 wherein the solid support is CPG and less than about $3\times10^{-3}$ mol of nucleoside is used per 25 g of CPG.

18. The method of claim 17 wherein about 2 to about 3 moles of diisopropylcarbodiimide are used per mole of nucleoside.

19. The method of claim 18 wherein the amount of N-hydroxybenzotriazole or nitrohydroxybenzotriazole, or combination thereof is about 0.1 times that of the diisopropylcarbodiimide.

20. The method of claim 15 wherein the solvent comprises about 5% or less pyridine.

21. The method of claim 20 wherein the solid support is CPG and less than about $3\times10^{-3}$ mol of nucleoside is used per 25 g of CPG.

22. The method of claim 21 wherein about 2 to about 3 moles of diisopropylcarbodiimide are used per mole of nucleoside.

23. The method of claim 22 wherein the amount of N-hydroxybenzotriazole or nitrohydroxybenzotriazole, or combination thereof is about 0.1 that of the diisopropylcarbodiimide.

24. The method of claim 15 wherein the solvent contains no pyridine.

25. The method of claim 24 wherein the solid support is CPG and less than about $3\times10^{-3}$ mol of nucleoside is used per 25 g of CPG.

26. The method of claim 25 wherein about 2 to about 3 moles of diisopropylcarbodiimide are used per mole of nucleoside.

27. The method of claim 26 wherein the amount of N-hydroxybenzotriazole or nitrohydroxybenzotriazole, or combination thereof is about 0.1 that of the diisopropylcarbodiimide.

* * * * *